United States Patent [19]

Johnson et al.

[11] Patent Number: 4,665,273

[45] Date of Patent: May 12, 1987

[54] ISOMERIZATION OF HIGH SULFUR CONTENT NAPHTHAS

[75] Inventors: James A. Johnson, Clarendon Hills; Robert J. Schmidt, Rolling Meadows, both of Ill.

[73] Assignee: UOP Inc., Des Plaines, Ill.

[21] Appl. No.: 829,338

[22] Filed: Feb. 14, 1986

[51] Int. Cl.$^4$ ................................................ C07C 5/24
[52] U.S. Cl. ................................... 585/739; 208/138; 585/750; 585/751
[58] Field of Search ...................... 585/739, 750, 751; 208/138

[56] References Cited

U.S. PATENT DOCUMENTS

| | | | |
|---|---|---|---|
| 3,461,062 | 8/1969 | Hansen | 208/89 |
| 3,507,931 | 4/1970 | Morris et al. | 585/739 |
| 3,531,243 | 9/1970 | Aitken et al. | 423/329 |
| 3,761,535 | 9/1973 | Sieg | 260/676 |
| 3,932,554 | 1/1976 | Takase et al. | 585/739 |
| 4,400,576 | 8/1983 | den Otter | 585/739 |
| 4,401,558 | 8/1983 | Pellet et al. | 208/65 |
| 4,489,216 | 12/1984 | Lewis | 585/739 |

OTHER PUBLICATIONS

Pfefferle, "The Reaction Chemistry of Catalytic Reforming, I. The Role of Sulfur", Presented before the Division of Petroleum Chemistry, Inc., American Chemical Society, Houston Meeting, Feb. 22-27, 1970.

*Primary Examiner*—Curtis R. Davis
*Attorney, Agent, or Firm*—Thomas K. McBride; John F. Spears, Jr.

[57] ABSTRACT

This invention relates to a process for isomerization of sulfur containing isomerizable hydrocarbons, especially saturated hydrocarbons having from 4 to 7 carbon atoms per molecule. More specifically, this invention relates to a process for isomerizing a sulfur containing combined feed where the sulfur compounds are controlled to achieve a level of from about 5 wt. ppm to about 150 wt. ppm utilizing a catalyst composition containing a hydrogen form crystalline aluminosilicate, a Group VIII metal, a refractory oxide and having a surface area of at least 580 m$^2$/g.

11 Claims, 2 Drawing Figures

ISOMERIZATION OF HIGH SULFUR CONTENT NAPHTHAS

BACKGROUND OF THE INVENTION

This invention concerns a process for isomerizing sulfur contaminated isomerizable hydrocarbons including paraffins and cycloparaffins. More particularly, this invention concerns a process for isomerizing an admixture of process streams, hereinafter referred to as the combined feed stream containing $C_4$-$C_7$ hydrocarbons, hydrogen and sulfur utilizing a catalytic composite comprising a hydrogenation component selected from the Group VIII noble metals, a hydrogen form crystalline aluminosilicate, and a refractory inorganic oxide.

The isomerization of low molecular weight normal paraffins is well established in the art. This reaction is of considerable importance in the petroleum industry because of the substantially higher octane number of isoparaffins compared to their normal paraffin counterparts. Since gasoline blends require a distribution of boiling range materials, the isoparaffins in the $C_4$-$C_7$ range are valuable blending components. A blend of various isomeric paraffins provides a gasoline which has a higher octane number than a gasoline consisting of normal paraffins. Isomerization is generally performed by passing light straight run (LSR) naphtha together with hydrogen through a reaction zone containing an isomerization catalyst. These LSR naphthas, containing primarily saturated $C_5$ and $C_6$ hydrocarbons, are commonly obtained from a refinery atmospheric distillation column and can contain sulfur compounds of various types in levels as high as 200 wt. ppm. As a result, conventional paraffin isomerization technology requries that feedstocks containing these levels of sulfur compounds be hydrotreated or otherwise desulfurized prior to exposure to the isomerization catalyst. However, this pretreatment of the feed represents additional capital and operating costs that can make upgrading LSR naphtha an uneconomical option. Thus, an isomerization process which can process sulfur containing feeds would result in a more efficiently produced and economically desirable high octane value product.

It has been the practice up until this time to isomerize paraffins to equilibrium mixtures of their branched chain isomers with a variety of catalysts. Friedel-Crafts catalysts, such as aluminum chloride, are known to be effective isomerization catalysts. Noble metals, such as platinum supported on halogenated alumina or silica alumina have also been used effectively to isomerize hydrocarbons. More recently, crystalline aluminosilicate zeolites which have shown catalytic activity have been effectively used in the isomerization of hydrocarbons. Both natural and synthetic crystalline aluminosilicates have been employed. Included among these are the Type X and Type Y zeolites as well as synthetic mordenite.

Specifically, the zeolites known as mordenites have received great attention. Mordenites are crystalline natural or synthetic zeolites of the alumino-silicate type; generally, they have a composition expressed in moles of oxide of

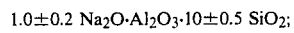

the quantity of $SiO_2$ may also be larger. Other alkali metals and/or alkaline earth metals may be substituted for all or part of the sodium.

In general, it has been found that the sodium form of mordenite is not particularly effective for isomerization of hydrocarbons and that replacing all or, for the greater part, the sodium cations with hydrogen ions yields the more advantageous hydrogen form mordenite. Conversion of the sodium form to the hydrogen form can be accomplished by a number of means. One method is the direct replacement of sodium ions with hydrogen ions using an acidified aqueous solution where the process of ion exchange is employed. Another method involves substitution of the sodium ions with ammonium ions followed by decomposition of the ammonium form using a high temperature oxidative treatment.

The activity and selectivity of hydroisomerization catalysts depend on a variety of factors, such as the mode of catalyst preparation, the presence or absence of promotors, quality of raw materials, feedstock quality, process conditions, and the like. Suitable catalysts can be conventionally prepared by combining commercially available crystalline zeolites, such as, a hydrogen form mordenite, with a suitable matrix material followed by the addition of a Group VIII metal, and thereafter activating by conventional means.

The process of isomerizing hydrocarbons containing high levels of sulfur can now be effectively accomplished utilizing a catalyst of novel composition. As exemplified within the instant application, this catalyst demonstrates superior isomerization performance compared to conventional isomerization catalysts when processing feeds containing sulfur.

OBJECTS AND EMBODIMENTS

Accordingly, there is provided a process for isomerization of sulfur containing isomerizable hydrocarbons wherein a combined feed having a controlled sulfur content from about 5 wt. ppm to about 200 wt. ppm is contacted under isomerization conditions with an isomerization catalyst. This catalyst comprises a Group VIII metal, hydrogen form aluminosilicate and refractory inorganic oxide, with the essential feature that the catalyst have a surface area of at least 580 m$^2$/g. One preferred method of controlling the sulfur content of the combined feed is by having no recycle of hydrogen from a product separation facility. Another preferred method for controlling the sulfur is by subjecting a recycle hydrogen stream from a product separation facility to a sulfur removal process prior to addition to the combined feed.

Platinum is the preferred Group VIII metal, and is preferably present in the amount of from 0.15 to 0.5 wt. % of said composite. The preferred hydrogen-form alumino-silicate has a silica to alumina ratio of at least 16 and is present in amounts from 75 to 95 wt. % of said composite and it most preferably has a mordenite structure. The preferred refractory inorganic oxide is alumina, particularly gamma-alumina, eta-alumina, or mixtures thereof.

The preferred isomerization process conditions employing the instant catalytic composite comprise a temperature range from about 200° F. to 800° F., a pressure of from about 100 to 1,000 psia and a liquid hourly space velocity in the range of 0.25 to 5 hr$^{-1}$. Hydrogen is also required in the amount ranging from 0.5 to 5 mole $H_2$/mole hydrocarbon feed.

These, as well as other embodiments of the present invention, will become evident from the following, more detailed description.

INFORMATION DISCLOSURE

The prior art recognizes a myriad of process schemes to reduce the sulfur content of hydrocarbon feedstocks prior to conversion into desirable products. Sulfur reduction to levels less than 1 wt. ppm is the aim of the methods taught. This low sulfur level is needed primarily because of the sensitivity to sulfur of the catalysts in the downstream processes.

The majority of prior teachings relate to the removal of sulfur from naphtha feedstocks using conventional hydrotreating prior to processing in a catalytic reforming process. The end product of such process schemes is gasoline quality reformates. U.S. Pat. No. 3,461,062 (Hansen) is representative of these prior teachings. Here, a hydrocarbon charge stock contaminated with sulfurous compounds is combined with hydrogen and contacted with a hydrofining catalyst to convert the sulfurous compounds to $H_2S$. The $H_2S$ is removed in a separation step prior to introducing the effluent from the hydrofining reaction zone to a catalytic reforming reaction zone.

In U.S. Pat. No. 3,761,535 (Sieg) a process is taught for converting butane and hexane into isopentane. Included in the process is the isomerization of a normal hexane stream containing at least 5 ppm sulfur compounds. Like the reference discussed above, the '535 patent is for a two-step process, one for isomerization and one for averaging. No control of the sulfur level is taught nor is any advantage to processing a sulfur-containing feed exemplified.

BRIEF DESCRIPTION OF THE DRAWINGS

Reference to the accompanying drawing will facilitate understanding of the present invention. The graph shown FIG. 1 of drawing illustrates the relationship between the Research octane (RON-O) value of the $C_5+$ isomerization product and the average catalyst bed temperature in the reactor. This RON-O value is also compared in FIG. 2 $C_5+$ isomerization product yield, measured as liquid volume percent on a fresh feed basis.

DETAILED DESCRIPTION

Figure 1:
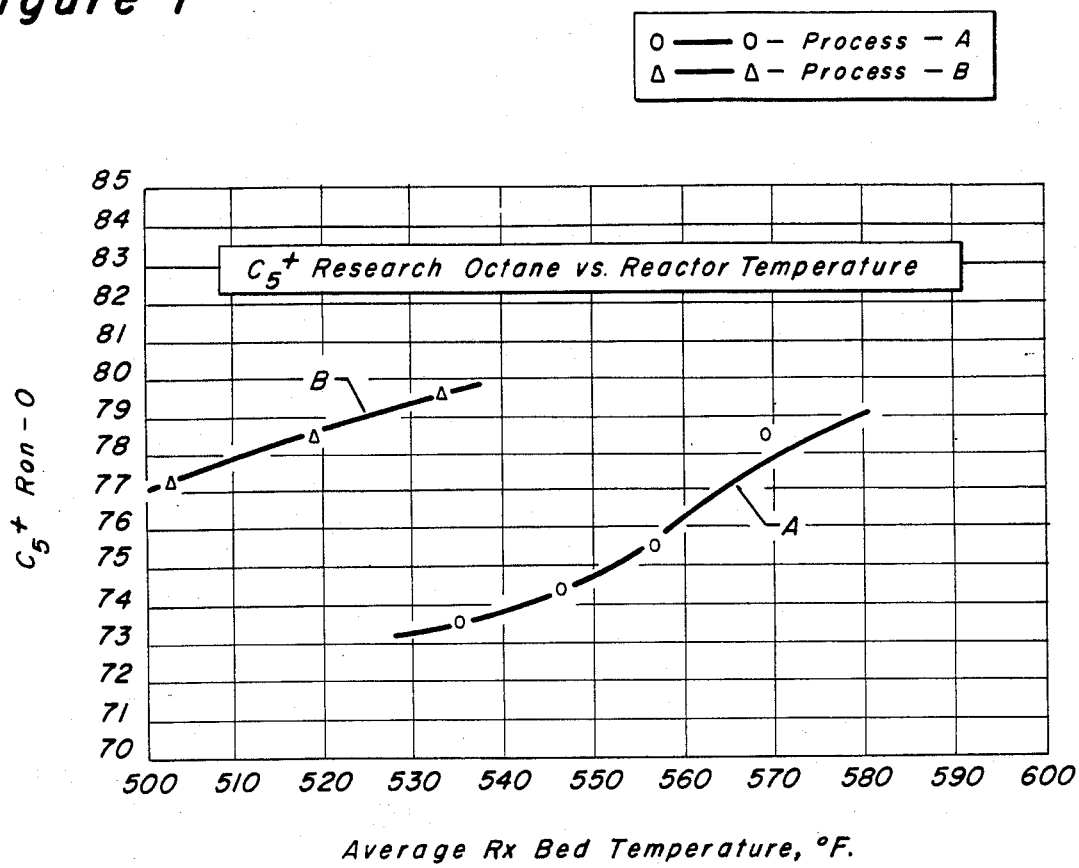

The process of this invention is applicable to isomerizable hydrocarbons including acyclic paraffins and cyclic naphthenes. It is applicable to straight or partially branched chain paraffins such as normal butane, normal pentane, normal hexane, normal heptane, normal octane, 2 methylpentane, 3 methylpentane, 3 ethylpentane, etc. It is also applicable to cycloparaffins such as alkylcyclopentanes and cyclohexanes, and methyl cyclopentane, dimethyl cyclopentane, cyclohexane, methyl cyclohexane, dimethyl cyclohexane, etc. The present inventive process is also applicable to mixtures of paraffins and/or naphthenes, including those derived from selective fractional distillation of natural gasolines and naphtha. Examples of such mixtures of paraffins and/or naphthenes include the so-called pentane fractions, hexane fractions, and mixtures thereof. This invention is not limited in its application to the enumerated saturated hydrocarbons. It is contemplated that straight or branched chain saturated hydrocarbons containing up to about 20 carbon atoms per molecule may be isomerized within the scope of the present invention. A preferred class of isomerizable hydrocarbons include those hydrocarbons having four to seven carbon atoms per molecule.

Straight-run hydrocarbons applicable to the process of this invention usually contain sulfur compounds in an amount ranging from about 1 wt. ppm to about 300 wt. ppm, calculated as elemental sulfur. It is a preferred embodiment of the instant case that the combined feed to the isomerization reaction zone contain $H_2S$ and/or organic sulfur compounds in an amount to provide an elemental sulfur content from about 5 wt. ppm to about 200 wt. ppm. The term "combined feed" as used herein means an admixture of process streams to be contacted with the isomerization catalyst. These process streams include fresh isomerizable hydrocarbons, recycled isomerizable hydrocarbons, $H_2$-rich light hydrocarbons, recycled $H_2$-rich light hydrocarbons and/or any other compounds which are desired to be added to the isomerization reaction zone. The term "$H_2$-rich light hydrocarbons" as used herein means a process stream containing at least 50 mole % $H_2$ with the balance being $C_1$–$C_3$ hydrocarbons. Recycled $H_2$-rich light hydrocarbons are commonly obtained from the product separation facilities of the isomerization process.

The sulfur level of the combined feed can exceed the preferred maximum level of 200 wt. ppm when sulfur build-up occurs. This is a result of recycling $H_2$-rich light hydrocarbons containing measurable quantities of sulfur, typically in the form of $H_2S$. The $H_2S$ is formed when sulfur compounds associated with the isomerizable hydrocarbons are converted in the isomerization reaction zone. Consequently, the $H_2S$, because of its high volatility, is separated concurrently with the $H_2$-rich light hydrocarbons in the product separation facilities. As more and more sulfur compounds are converted to $H_2S$ in the reaction zone the level of $H_2S$ in the recycle stream will constantly increase to an equilibrium level consistent with product separator operation conditions. Thus, as the recycle stream is admixed with the other process streams making up the combined feed, the total sulfur content of the combined feed will increase to a level 20 to about 80% greater than the fresh feed sulfur level depending on the separator temperature and pressure.

Accordingly, an embodiment of the present invention is the control of the combined feed sulfur level within the range of from about 5 to 150 wt. ppm. Any control means known in the art can be used, including catalytic conversion, physical or chemical adsorption, physical separation and the like. One preferred method of control involves having no recycle of $H_2$-rich light hydrocarbons from a product separation facility. This scheme would prevent the occurrence of sulfur build-up as described above. Another preferred method to control the sulfur level of the combined feed is by subjecting recycled $H_2$-rich light hydrocarbons to a sulfur removal process prior to addition to the combined feed. This removal process may reduce or eliminate the sulfur compounds from the recycled $H_2$-rich light hydrocarbons by any means known in the art including adsorption processes, catalytic processes, or combinations thereof. Adsorption processes may employ molecular sieves, high surface area silica-aluminas, carbon molecular sieves, crystalline aluminosilicates, activated carbons, and the like. Catalytic processes may employ traditional sulfur reducing catalyst formulations known to the art including refractory inorganic oxide supports containing metals selected from the group comprising Group VIB, Group IIB, and Group VIII metals. The amount of sulfur control can be varied to obtain the desired sulfur level in the combined feed. Low levels of sulfur in the fresh isomerizable hydrocarbons (5-150 ppm) requires no sulfur removal from the recycled $H_2$-rich light hydrocarbons as sufficiently low levels of recycle $H_2S$ (<100 ppm) can be maintained via losses of $H_2S$ in the product separator liquid and conversely a high level of sulfur in the fresh isomerizable hydrocarbon (<150 ppm) may require sulfur removal from the recycled $H_2$-rich light hydrocarbons.

The catalyst composition of the present invention comprises a Group VIII noble metal, hydrogen form crystalline aluminosilicate, and a refractory inorganic oxide with said catalyst composition having a surface area of at least 580 $m^2/g$. We have found that significant improvements in isomerization performance are realized when the surface area of the catalytic composition is at or above 580 $m^2/g$.

The metal that is incorporated into the catalytic composite to supply the hydrogenation-dehydrogenation function is a Group VIII noble metal. The Group VIII noble metals include the metals of the "Platinum Series" and the metals of the "Palladium Series", i.e., platinum, iridium, osmium, palladium, rhodium, and ruthenium. The preferred Group VIII noble metal is platinum. The Group VIII noble metal of the catalytic composition of the present invention will be utilized in an amount from about 0.05 to about 5% by weight of the composite. It is particularly preferred that the metal component be at least about 0.15% by weight and not over 0.5% by weight.

Of course, it is not beyond the scope of the instant invention that the catalytic composition contain, in addition to the Group VIII noble metal, a catalytically effective amount of a promoter metal. Examples of such promoter metals include tin, lead, germanium, cobalt, nickel, iron, tungsten, chromium, molybdenum, bismuth, indium, gallium, cadmium, zinc, uranium, copper, silver, gold, tantalum, one or more of the rare earth metals and mixtures thereof.

The crystalline aluminosilicate of the present invention is a hydrogen form silica-alumina having either a three-dimensional or channel-pore-structure crystal lattice framework. The three-dimensional aluminosilicates include both synthetic and naturally occurring silica aluminas, such as, the faujasites which include X-type, Y-type, ultrastable-Y and the like. L-type, omega-type, and mordenite are examples of the channel-pore-structure crystalline aluminosilicates.

The aluminosilicate material that is preferred in the catalytic composition of this invention is the particular form of aluminosilicate material known as mordenite. While mordenite is naturally occurring, a variety of synthetic mordenites are available commercially, usually in a powder form. These synthetic mordenites can be obtained in both the sodium form and hydrogen form and at varied silica to alumina ratios. It is a preferred embodiment of the present invention that the mordenite be of the hydrogen form and that the silica to alumina ratio be at least 16:1, more specifically, in the range from 16:1 to 60:1.

The hydrogen form aluminosilicate is incorporated with a refractory inorganic oxide and formed into a catalyst composite. The formed catalyst composite may be prepared by any known method in the art including the well-known oil drop and extrusion methods. The hydrogen form aluminosilicate may be present in an amount within the range of 50 to about 99.5 weight percent, preferably within the range of 75 to about 95 weight percent, and the refractory inorganic oxide may be present in an amount within the range of from 0.5 to about 50 percent.

The preferred inorganic oxide for use in the present invention is alumina. The alumina is preferably selected from the group consisting of gamma-alumina, eta-alumina and mixtures thereof. Other refractory inorganic oxides which are contemplated include, for example, silica gel, silica-alumina, magnesia-alumina, zirconica alumina, phosphorus containing alumina, and the like.

It has been found that a strong correlation exists between the isomerization performance of a catalyst composite of the subject invention and the surface area of said composite. One preferred method to achieve maximum isomerization performance is by utilizing formed catalytic composites with surface areas measuring at least 580 $m^2/g$. Surface area, as referred to herein, is determined by employing the Langmuir method of correlating adsorption/desorption isotherm data. The Langmuir method is especially suitable for catalytic composites containing high percentages of crystalline aluminosilicates. The data needed for the Langmuir method is typically obtained by well known adsorption/desorption apparatuses, preferably a nitrogen adsorption/desorption apparatus. Any method may be employed which results in a final catalyst composite having at least a surface area of 580 $m^2/g$.

The catalyst of the invention has particular utility for the isomerization of isomerizable hydrocarbons. Included in the group of isomerizable hydrocarbons are saturated hydrocarbons, more particularly straight chain or slightly branched chain paraffins containing four or more carbon atoms per molecule. The isomerization reaction can be conducted over a wide range of temperatures, but, in general, in the range from about 93° C. (200° F.) to about 427° C. (800° F.). Space velocities from about 0.25 to about 5 liquid volumes per hour of said isomerizable hydrocarbons per volume of said catalytic composite are preferred with reaction zone pressures preferably within the range from about 6.9 bar (100 psi) to about 69 bar (1000 psi). It is particularly desirable to carry out the isomerization reaction in the presence of hydrogen preferably in the range from about 0.5 to about 5 moles of $H_2$ per mole of isomerizable hydrocarbon. The function of the hydrogen is primarily to improve catalyst life, apparently by preventing polymerization of intermediate reaction products which would otherwise polymerize and deposit on the catalytic composite. It is not necessary to employ pure hydrogen since hydrogen containing gases are suitable. Product separation facilities of the isomerization process or other processes, such as catalytic conversion of naphthas are suitable sources of $H_2$-rich gases. These $H_2$-rich gases typically contain light hydrocarbons, $C_1$-$C_3$, and may also contain other compounds including sulfur.

The following example is presented for purposes of illustration only and is not intended to limit the scope of the present invention.

EXAMPLE I

Two isomerization process tests were conducted to study how sulfur containing feedstocks affect isomerization performance. The first process, designated as Process A, utilized an isomerization catalyst having a surface area not in accordance with the subject invention. Process A was tested to demonstrate the isomerization performance when a sulfur containing feed is subjected to a conventional isomerization catalyst of the prior art. This catalyst was prepared in the following manner. A 9:1 weight ratio mixture of hydrogen form, low sodium, partially dealuminated synthetic mordenite powder (marketed by Union Carbide under the name LS-M-8) and alumina was admixed with an acidified peptization solution and extruded by means known in the art. The extruded composite was dried, calcined in an oxidative atmosphere, impregnated with platinum, and calcined again. The platinum was added to a level of 0.324 wt. %, based on the weight of the finished catalyst. A surface area of 567 $m^2/g$ was measured for this catalyst.

The second process, designated as Process B, was in accordance with the present invention and utilized a catalyst that was formulated substantially in the same manner as the catalyst in Process A. However, in accordance with the subject invention, the dried extrudate prior to calcining and platinum addition was contacted with an acidic aqueous solution containing ammonium ions. This solution contained 10 wt. % HCl and 10 wt. % $NH_4Cl$. Contacting of the solution and the extrudate was performed at 140° F. (60° C.) for 120 minutes at a solution to zeolite weight ratio fo 25:1. The extrudate was subsequently dried, calcined and treated with platinum following the same procedures used for the catalyst in Process A. The catalyst of Process B had a platinum level of 0.308 wt. % and a surface area of 630 $m^2/g$.

Processes A and B were evaluated for isomerization performance in a flow reactor processing a feed comprising a mixture of 6.8 wt. % butane, 20.9 wt. % n-pentane, 14.5 wt. % i-pentane, 15.7 wt. % n-hexane, 19.0 wt. % i-hexane, 12.4 wt. % cyclopentanes/cyclohexanes and 2.5 wt. % benzene, 8.2 wt. % $C_6^+$, and 133 wt. ppm sulfur.

Figure 2:
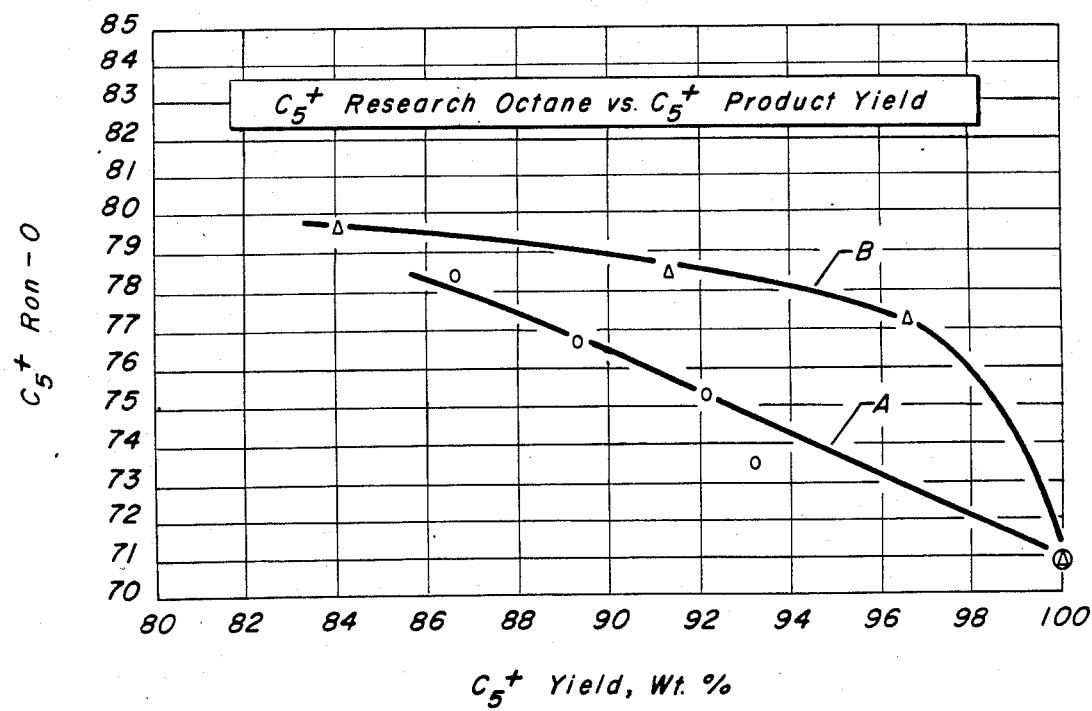

The operating conditions used to test the isomerization performance of Processes A and B comprised a reactor pressure of 32.0 bar (450 psig), a liquid hourly space velocity of 1.0 $hr^{-1}$, a $H_2$ to feed hydrocarbon molar ratio of 2.0 and temperatures ranging between 254° C. (490° F.) and 316° C. (600° F.). The Research octane value (RON-O) of the $C_5^+$ liquid product, the average reactor catalyst bed temperature, and the weight percent $C_5^+$ yield were used to determine isomerization performance. The RON-O is shown in the attached drawing as a function of both the average reactor bed temperature and the $C_5^+$ yield. The process of the instant invention, Process B, has a significant activity advantage over the conventional isomerization process, Process A, employing a prior art catalyst. This is illustrated in FIG. 1 by the 58° F. lower temperature requirement to achieve 78 RON-O. Process B also exhibits a significant octane advantage of up to four numbers at 94 wt. % $C_5^+$ yield, compared to Process A, as shown in FIG. 2.

These examples clearly demonstrate the superior performance of the subject invention when compared to the isomerization performance obtained with a conventional process employing a prior art catalyst. A comparison at equivalent product yields shows the invention of the instant application to have higher isomerization activity with an increased product octane value. Conversely, a comparison at equivalent product octane (e.g., 78 RON) shows the invention of the instant application to have a greater product yield.

We claim:

1. An isomerization process which comprises contacting a combined feed comprising sulfur compounds, isomerizable hydrocarbons and $H_2$ under isomerization conditions with an isomerization catalyst, controlling the amount of sulfur compounds in the combined feed to achieve an elemental sulfur level of from about 5 wt. ppm to about 200 wt. ppm, said catalyst comprising a Group VIII noble metal, hydrogen form mordenite and a refractory oxide and having a surface area of at least 580 $m^2/g$.

2. The process of claim 1 further characterized in that the combined feed comprises saturated hydrocarbons having 4 to 7 carbon atoms per molecule and molecular hydrogen in an amount to achieve a hydrogen to hydrocarbon mole ratio of 0.5–5 moles of hydrogen/mole of saturated hydrocarbons.

3. The process of claim 1 further characterized in that the combined feed elemental sulfur level is controlled by having no recycle of $H_2$-rich light hydrocarbons from a product separation facility.

4. The process of claim 1 further characterized in that the combined feed elemental sulfur level is controlled by subjecting recycled $H_2$-rich light hydrocarbons from a product separation facility to a sulfur removal process prior to addition to the combined feed.

5. The process of claim 4 further characterized in that the sulfur removal process comprises an adsorption process utilizing molecular sieves or other adsorption medium.

6. The process of claim 4 further characterized in that the sulfur removal process comprises a catalytic process utilizing a refractory inorganic oxide support containing metals selected from the group comprising Group VIB and Group VIII metals.

7. The process of claim 1 wherein the Group VIII noble metal is platinum and is present in an amount of from 0.15 to 0.5 wt. percent of the catalyst.

8. The process of claim 1 wherein the hydrogen form crystalline aluminosilicate has a silica to alumina ratio of at least 16:1.

9. The process of claim 1 wherein the hydrogen form crystalline aluminosilicate is present in an amount of from 75 to 95 percent by weight of the catalyst.

10. The process of claim 1 wherein the refractory inorganic oxide is alumina, selected from the group consisting of gamma-alumia, eta-alumina, and mixtures thereof.

11. The process of claim 1 further characterized in that the isomerization conditions include a temperature in the range of from about 200° F. to about 800° F., a pressure of from about 100 to about 1000 pounds per square inch, a liquid hourly space velocity of from about 0.5 to about 5 liquid volumes of said isomerizable hydrocarbons per hour per volume of said catalyst and a hydrogen to hydrocarbon mole ratio of 0.5–5 mole of $H_2$/mole of isomerizable hydrocarbon.

* * * * *